United States Patent [19]

Heine et al.

[11] Patent Number: 5,542,904
[45] Date of Patent: Aug. 6, 1996

[54] HANDGRIP FOR AN ELECTRO-OPTICAL DIAGNOSTIC APPARATUS SET

[75] Inventors: Helmut Heine; Otto H. Schmidt, both of Herrsching; Gerhard Gügel, Diessen; Norbert Merkt, Breitbrunn; Arno Zirnheld, Gilching, all of Germany

[73] Assignee: Heine Optotechnik GmbH & Co. KG, Herrsching, Germany

[21] Appl. No.: 293,298

[22] Filed: Aug. 22, 1994

[30] Foreign Application Priority Data

Aug. 30, 1993 [DE] Germany .............................. 9313009 U

[51] Int. Cl.⁶ .................................. A61B 1/26; F21L 7/00
[52] U.S. Cl. ...................... 600/197; 600/185; 600/193; 600/200; 600/249; 600/199; 362/194; 362/804
[58] Field of Search ..................................... 600/185, 193, 600/197, 198, 199, 200, 247, 248, 249; 362/183, 194, 195, 196, 202, 804

[56] References Cited

U.S. PATENT DOCUMENTS

| | | |
|---|---|---|
| 3,595,222 | 7/1971 | Vellacott et al. . |
| 3,597,051 | 8/1971 | Copeland et al. . |
| 3,638,644 | 2/1972 | Reick . |
| 3,643,083 | 2/1972 | Heine . |
| 3,826,248 | 7/1974 | Gobels . |
| 4,574,784 | 3/1986 | Soloway . |
| 4,669,449 | 6/1987 | Baumann . |
| 4,884,558 | 12/1989 | Gorski et al. . |
| 5,003,962 | 4/1991 | Choi . |
| 5,008,785 | 4/1991 | Maglica et al. . |
| 5,153,495 | 10/1992 | Connors .............................. 362/183 X |
| 5,177,424 | 1/1993 | Connors ........................................ 320/2 |

FOREIGN PATENT DOCUMENTS

| | | |
|---|---|---|
| 2078644 | 11/1992 | Canada . |
| 0339541A1 | 11/1989 | European Pat. Off. . |
| 824662 | 12/1951 | Germany . |
| 2147054 | 4/1973 | Germany . |
| 2738202C2 | 3/1979 | Germany . |
| 2852956 | 6/1980 | Germany . |
| 3007831C2 | 9/1981 | Germany . |
| 3317832C2 | 6/1984 | Germany . |
| 3742268C2 | 6/1989 | Germany . |
| 327644 | 2/1968 | U.S.S.R. . |

Primary Examiner—Richard J. Apley
Assistant Examiner—Beverly M. Flanagan
Attorney, Agent, or Firm—Griffin, Butler, Whisenhunt & Kurtossy

[57] ABSTRACT

A handgrip for an electro-optical diagnostic-device set comprises a tubularly-shaped battery housing (10) for receiving variously-shaped energy sources (31, 33, 36, 38) therein to energize a lamp of an instrument head at a second end of the tubularly-shaped battery housing. There is a set of releasable end covers 40 for an opposite, first, end of the tubularly-shaped battery housing, with each of the end covers having a substantially identical cover attaching element (42) as that of the other end covers for mating with an opposite housing attaching element of the housing, but with each end cover being shaped differently from the other end covers, so as to accommodate an energy source different from energy sources accommodated by the other end covers.

5 Claims, 2 Drawing Sheets

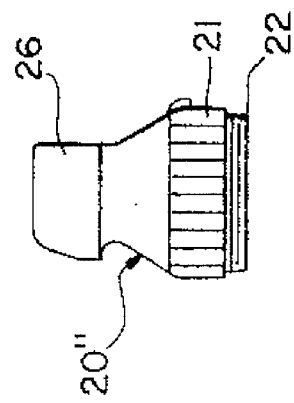
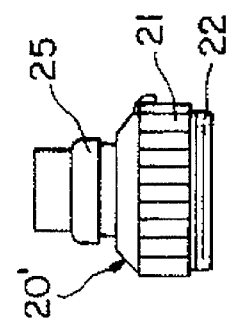
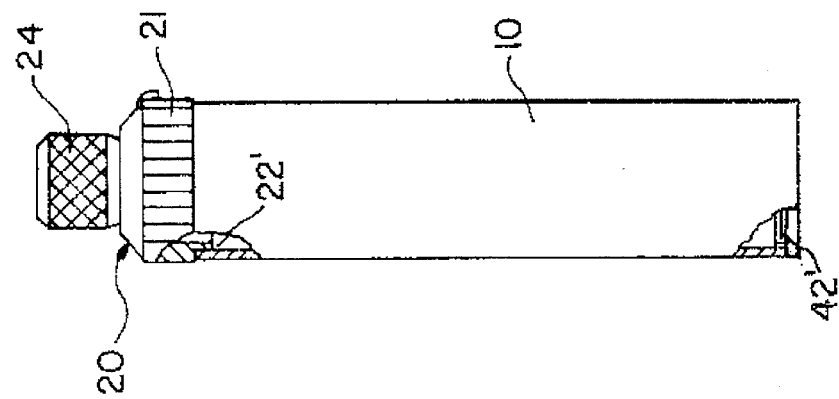

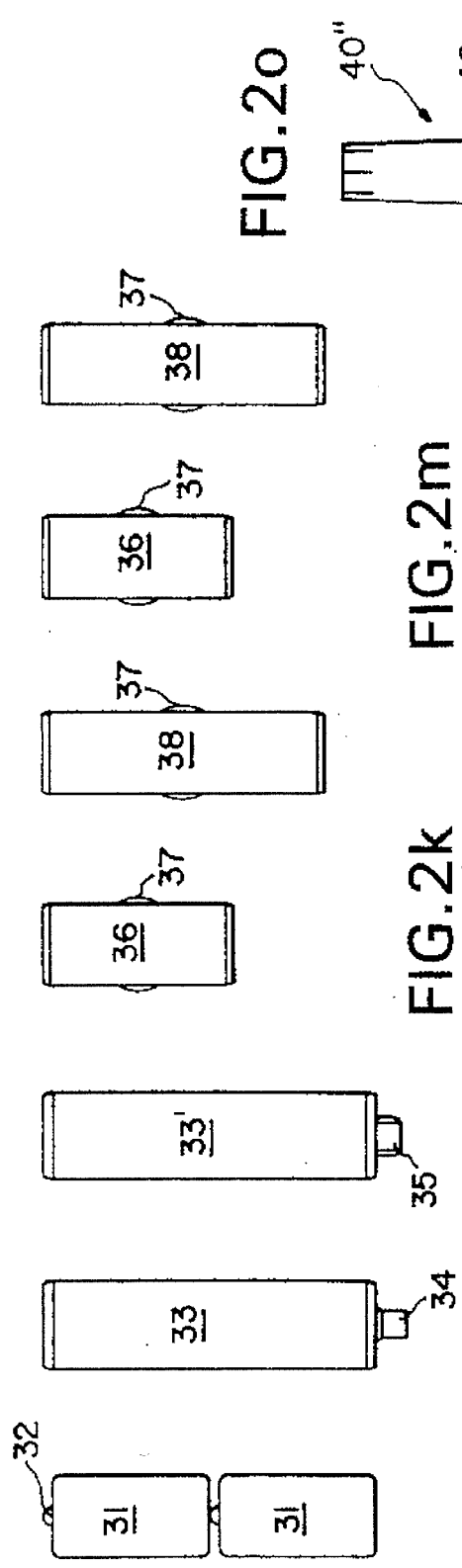

HANDGRIP FOR AN ELECTRO-OPTICAL DIAGNOSTIC APPARATUS SET

BACKGROUND OF THE INVENTION

This invention concerns a handgrip for an electro-optical diagnostic-device set with a tubularly-shaped battery housing for receiving an energy source (in the form of one or more batteries or a battery accumulator) of various lengths (depending upon need or availability) to energize a lamp, the battery housing having a releasably attached end cover, at one end and, a releasably attached coupling piece for receiving an instrument head such as an otoscope, ophthalmoscope, laryngoscope or the like at the other end.

There are many hand held instruments to examine body surfaces and natural body openings for making medical diagnoses. These instruments have in common, among other things, that they include a small light source, such as an incandescent lamp, for illuminating places to be examined. Particularly because of the desirability of using such devices away from particular facilities, handgrips with batteries therein are often used to energize such instruments. So that each such instrument does not need its own handgrip, coupling pieces between the handgrip and instrument attachments, or accessories, are either standardized or so formed during their manufacture that various attachments can be used on the same grip.

In order to serve the needs and customs of users, such handgrips are usually offered for two or three primary, or normal, battery cells or also for chargeable batteries with two or three cells. Among the so called chargeable grips one must also distinguish between those which must be placed in a charging apparatus and receive their charging supply via outwardly facing contacts, those with coupling plugs to be charged with reduced alternating voltage (for example, in the form of a so called receptacle transformer), and those with a house current plug to be coupled to a power company receptacle.

Despite the standardizing of connections at instrument ends, a large number of various grips, whose measurements are determined by types of batteries used and types of charging employed, are still necessary. Manufacturing and storage, by manufacturers as well as during medical distribution, are correspondingly difficult and expensive. A user must, among other things, acquire a new grip if he wants to change the type of batteries or battery supply used. This is often the case during hospital rounds or during off-site patient visits. If a battery charge of a chargeable grip is thereby prematurely exhausted, there is no possibility of quickly recharging it. A desired chargeable grip can also not be used with primary, or ordinary, battery cells, and vice versa, without taking some steps.

A handgrip for use with an electro-optical diagnostic-device set of the type described in the opening paragraph above is known from CA-A-2 078 644 in which a coupling piece is formed such that it can be adapted to different lengths of two primary cells on the one hand and three cells of an accumulator on the other hand. It comprises a tubular member whose actual coupling member couples with an instrument head on one side and into which an adapter is screwed on the other side. For use with simple non-chargeable batteries, the adapter receives proximally part of a battery and leads a plus pole thereof out of the other side where a terminal pin mounted on the coupling piece makes contact with a foot, or center, contact of a lamp. For use with an accumulator, a transformer and a rectifier are in the adapter. Two male plugs extend into the interior of the tubular member for being guided into a receptacle, while at another, proximal side, a central contact extends outwardly, on which a central pole, or terminal, of the accumulator lies. A third embodiment of the adaptor allows coupling to an external charging device having a transformer and a rectifier via a reduced-voltage coupling cable.

In the known device set a structural length of handgrip is relatively great while in each case the male plugs of the second embodiment must be received in the coupling piece. The structural length of this member is for other energy sources, for example non-chargeable batteries, excessive. Further, various adaptors having substantial structural differences must be held in readiness. This known handgrip finally fails completely when accumulators as well as batteries are to be used whose lengths deviate from those of the design.

It is an object of this invention to provide a handgrip for diagnostic-device sets which allows one to simplify and reduce manufacturing and storing costs of known handgrips of the type of this invention.

SUMMARY OF THE INVENTION

According to principles of this invention, a handgrip of the type described in the opening paragraph above has a plurality of end covers, each having a cover attaching element which is identical to those of the other covers for universally mating with an opposite housing attaching element of a battery housing, and with each cover, depending upon a type of energy source with which it is to be used, comprising an end cap or an end cap with one or more possibly adapting attachments of different lengths.

BRIEF DESCRIPTION OF THE DRAWING

The invention is described and explained in more detail below using the embodiments shown in the drawings. The described and drawn features, in other embodiments of the invention, can be used individually or in preferred combinations. The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 1a is a partially-cutaway side view of a tubularly-shaped battery housing having a coupling piece mounted on an end thereof;

FIGS. 1b and 1c are side views of various prior-art coupling pieces which can be used with the tubularly-shaped battery housing of FIG. 1a;

Each of FIGS. 2a–2c is a side view of one or more batteries of different types;

Each of FIGS. 2d–2g is a side view of a battery accumulator of a type which could be used with a tubularly-shaped battery housing employing a set of releasably-attached end covers of this invention;

FIGS. 2h–2o are side views of end covers forming a set of releasably-attached end covers of this invention; and FIGS. 2p–2v are end views of the end covers depicted in FIGS. 2h–2n.

DESCRIPTION OF THE PREFERRED EMBODIMENT

FIG. 1a shows a plan, elevational, view of a metallic, tubularly-shaped, battery housing 10 with, at one end, a screwed universal coupling piece 20 having a roughened screwing ring 21 which can be rotated to turn an incandescent lamp (not shown), mounted in the coupling piece 20 or in an instrument head, on and off. In FIGS. 1b and 1c male exterior threads 22 of coupling pieces 20' and 20" can be seen for mating with internal threads 22' of the battery housing 10. An attaching piece 24 shown in FIG. 1a serves as a universal coupling for a plurality of various, different-from-one-another, instrument attachments of a particular manufacturer, an attaching piece 25 of FIG. 1b being for widely used instrument attachments in North America and an attaching piece 26 of FIG. 1c being for attaching laryngoscope spatulas with their particular, mostly standard, flap mechanisms.

FIGS. 2a–2g show various embodiments of batteries and battery accumulators while FIGS. 2h–2v show corresponding end covers, with side views being in FIGS. 2h–2o and end views being in FIGS. 2p–2v.

The energy source of FIG. 2a comprises two simple primary battery cells 31 with a usual central plus pole, or terminal, 32 and a, not-visible, opposite, minus pole. FIG. 2h shows a corresponding end cover, or closure, 40 with an end cap 41, whose exterior, or male, threads 42 can be screwed into internal threads 42' of the tubularly-shaped battery housing 10. A normal contact spring 43 is attached at the inner side of the end cap 41. In an assembled state, the spring presses on the minus pole of the lower battery 31 while the plus pole 32 is in contact with the coupling piece 20. As shown in FIG. 2p a floor of the end cover 40 has no holes therein.

Each of FIGS. 2b and 2c respectively shows a battery accumulator 33 and 33' which, in the same manner as the cells 31 of FIG. 2a, fill out the entire length of the battery housing 10. Each of the battery accumulators 33, 33' has a circularly-shaped, or oval, terminal 34, 35, which extends through the spring 43 into a corresponding opening of the end cap 41 (see FIGS. 2b, 2q, 2c, 2r). Each of FIGS. 2d and 2f shows a battery accumulator 36 having a quite short structural length, there being provided on end surfaces of each a plus pole (not seen) and on a side surface two minus poles 37, which, after they are mounted, contact interior walls of the battery housing 10. Between each corresponding end cap 41 and its spring 43', there is a two part adapting piece, with a charging electronic circuit (FIG. 2k), or a charging transformer and a charging electronic circuit, being stored in a lower, wider adapting piece 44. In the embodiment of FIGS. 2d, 2k and 2s connections to the battery accumulator 36 are established by a coupling (not shown) to a terminal 46 having a circular cross-sectional shape. In the embodiment of FIGS. 2f, 2m and 2u plugs 47 serve to provide direct couplings to a normal electrical outlet receptacle. A portion 45 of the adapting piece serves only to bridge an empty space between the lower adapting piece 44 and the battery accumulator (or storage battery, or cell) 36.

A mounting coupling which allows an accumulator, either when charging or during battery use, to be used, is well known, for example, see German Patent Document DE-A-3 007 831.

The portion 45 can be eliminated if a battery accumulator of medium structural length should be used (see FIGS. 2e, 2l, 2g, and 2n).

Finally, FIG. 2o shows an end cover 40" with an empty adapting piece 44' to which an electrode 48 is affixed which bridges a space to the contact in the coupling piece 20. A supply voltage is provided by a connecting cable 49.

A battery hand grip of this invention can, as can be seen above, with only a few structural set-like parts forming end covers, be adapted for use with more-or-less-often-used batteries and battery accumulators. Only the adapting pieces 44, 45 and possibly the electrode 48 must be additionally held in readiness to be added to the basic shape of FIG. 2p.

A handgrip according to principles of this invention makes it further possible for one to economically change the type of battery, or battery like, element. With this invention one can at any time quickly switch from a desired chargeable battery to operation with a dry cell battery, and vice versa.

When used at a maximum structural length for a particular maximum number of primary cells, or a corresponding accumulator, the hand grip of this invention requires only a normal cap with a contact spring which produces a contact to a foot, or end, pole of the battery or accumulator. If in this embodiment an accumulator is charged by an external charging transformer the end cover is provided with a simple, substantially centrally located, two pole terminal. With a shorter structural length a space between the cap and a proximal end of the battery, or accumulator, can be bridged by the adapting attachments in which possibly a transformer and/or a charging circuit with a rectifier can be stored, which also can be coupled via a two pole terminal to a corresponding external voltage source. Receptacle plugs, or pins, can also be mounted on the outer surface of the end cover, however, if the handgrip is to be charged by plugging it directly into an electrical receptacle. If a supply voltage is directly led to a foot, or end, contact of a glow lamp, a bridging electrode is mounted on the end cover in an intermediate space between it and a foot contact of the lamp, or an intermediate contact, the electrode being supplied with a voltage via a coupling.

While the invention has been particularly shown and described with reference to a preferred embodiment, it will be understood by those of ordinary skill in the art that various changes in form and detail may be made therein without departing from the spirit and scope of the invention.

The embodiments of the invention in which an exclusive property or privilege are claimed are defined as follows:

What is claimed is:

1. A handgrip adaption set for an electro-optical apparatus set comprising:
    a tubularly-shaped battery housing for receiving any, energy source selected from a predetermined plurality of energy sources with different configurations for energizing a light source, said housing having a first housing attachment element at a first end thereof and a second housing attachment element at an opposite, second, end thereof;
    a set of interchangeable, releasably-attachable, end covers, each for being mounted to the first housing attachment element at the first end of the battery housing, said set of interchangeable releasably-attachable end covers including:
        at least a first end cover comprising a solid first end cap and a first contact spring attached at an inner side of the first end cap for making contact with a first energy source when it is in said battery housing and said first end cover is mounted at said first end of said battery housing;
        at least a second end cover comprising a second end cap with an opening therein and a second contact spring attached at an inner side of the second cap for making contact with a second energy source when it is in said battery housing and said second end cover is mounted at said first end of said battery housing;

at least a third end cover comprising a third end cap and a third contact spring for making contact with a third energy source when it is in said battery housing and said third end cover is mounted at said first end of said battery housing, said third energy source being substantially smaller than at least one of said other energy sources, wherein, said third end cover includes a third-cover adapting piece, including a charging electronic circuit for charging said third energy source, mounted between the third end cap and the third contact spring;

at least a fourth end cover comprising a fourth end cap, a fourth-cover adapting piece including a charging electronic circuit mounted on said fourth end cap, and a fourth contact spring supported by said fourth-cover adapting piece for making contact with a fourth energy source when it is mounted in said battery housing and said fourth end cover is mounted at said first end of said battery housing, said fourth energy source being substantially shorter than said third energy source, wherein said fourth end cover further includes an auxiliary fourth-cover adapting piece, with a smaller diameter than the diameter of the fourth-cover adapting piece, disposed between the fourth-cover adapting piece and the fourth contact spring to bridge an empty space between the fourth-cover adapting piece and the fourth energy source;

at least a fifth end cover comprising a fifth end cap with a two-pole plug thereon serving to provide a coupling for connection to a normal main electrical supply, a fifth contact spring and a fifth-cover adapting piece, including a charging electronic circuit, disposed between the fifth contact spring and the fifth end cap; and at least a sixth end cover comprising a sixth end cap with a two-pole plug serving to provide a coupling for connection to a normal main electrical supply, a sixth-cover adapting piece including a charging electronic circuit, a sixth contact spring, and an auxiliary sixth-cover adapting piece having a smaller diameter than the diameter of the sixth-cover adapting piece serving to bridge an empty space between the sixth-cover adapting piece and a sixth energy source when it is mounted in the battery housing and being disposed between the sixth contact spring and the sixth-cover adapting piece;

at least one releasably-attachable coupling piece for being mounted to the second housing attachment element at said opposite, second end of said battery housing for mounting a scope instrument head to said opposite, second, end of the battery housing;

wherein each end cover of said set of releasably-attachable end covers has a cover attachment element, adapted to mate with the said first housing attachment element.

2. A handgrip adaption set as in claim 1 wherein the first and second housing attachment elements at said opposite first and second ends of said battery housing are substantially identical in structure and wherein said at least one releasably-attachable coupling piece has a coupling-piece attachment element which is substantially identical in structure to the cover attachment elements.

3. A handgrip adaption set as in claim 2 wherein said first and second housing attachment elements are formed of threads at opposite ends of the battery housing and wherein the coupling-piece attachment element and the cover attachment elements are corresponding threads which mate with the threads of said first and second housing attachment elements.

4. A handgrip adaption set as in claim 1 wherein is included a seventh end cover having a seventh end cap and a bridging electrode on an inner surface of the seventh end cap to bridge a space between said coupling piece and said seventh end cap, and wherein said seventh end cover includes external two-pole terminals for providing a supply voltage to said coupling piece via said bridging electrode, said two-pole terminals being mounted on the outer side of said seventh end cap.

5. A handgrip adaption set as in claim 1 wherein are further included a plurality of differently configured scope instrument heads, each having the same attachment structure for mating with said coupling piece.

* * * * *